United States Patent [19]
Zappelli et al.

[11] 4,336,188
[45] Jun. 22, 1982

[54] METHOD FOR THE PREPARATION OF MACROMOLECULARIZED ADENINE DERIVATIVES

[75] Inventors: Piergiorgio Zappelli; Antonio Rossodivita; Rosario Pappa, all of Monterotondo; Luciano Re, Rome, all of Italy

[73] Assignee: Snamprogetti, S.p.A., Milan, Italy

[21] Appl. No.: 880,133

[22] Filed: Feb. 22, 1978

Related U.S. Application Data

[62] Division of Ser. No. 705,012, Jul. 14, 1976, Pat. No. 4,091,203.

[30] Foreign Application Priority Data

Jul. 15, 1975 [IT] Italy .............................. 25419 A/75
May 4, 1976 [IT] Italy .............................. 22958 A/76

[51] Int. Cl.³ .......................................... C07H 19/20
[52] U.S. Cl. ............................. 260/112.5 R; 536/26; 536/27; 536/28; 544/229; 544/276
[58] Field of Search ................. 544/276, 229; 536/26, 536/27; 260/112.5 R

[56] References Cited

U.S. PATENT DOCUMENTS 2,946,781  7/1960  Shunk et al. ..................... 536/26
3,989,812  11/1976 Barrett et al. ................ 260/112.5 R Primary Examiner—Paul M. Coughlan, Jr.
Attorney, Agent, or Firm—Morgan, Finnegan, Pine, Foley and Lee

[57] ABSTRACT

A method is disclosed for preparing functionalized adenine derivatives, said method comprising the step of reacting a compound which contains an adenine nucleus which has been halogen substituted in the 8-position, with a compound having the general formula $M^+ {}^-S-(CH_2)_n-COO^-M^+$ wherein $M^+$ is the ion of an alkali metal and n is an integer, the reaction being carried out in a polar aprotic solvent. Procedures for preparing macromolecularized adenine compounds are also indicated by reacting a functionalized adenine derivative with a polymer which has at least one primary or secondary aminic group in its structure.

5 Claims, No Drawings

METHOD FOR THE PREPARATION OF MACROMOLECULARIZED ADENINE DERIVATIVES

This is a division of application Ser. No. 705,012 filed July 14, 1976, U.S. Pat. No. 4,091,203.

This invention relates to a method for the preparation of functionalized adenine derivatives and to the products obtained thereby. More detailedly, the present invention relates to a method for the preparation, starting from compounds which contain an adenine nucleus having a halogen atom in the 8-position, of functionalized adenine derivatives carrying in said position an omega-carboxylic side chain. The starting materials for said method can be obtained, with conventional methods, by halogenating compounds which contain the adenine nucleus, such for example nicotinoylamide adenine dinucletide (NAD+), nicotinoylamideadenine dinucleotide phosphate (NADP+), adenosine triphosphate (ATP), adenosine diphosphate (ADP), adenosine monophosphate (AMP), adenosine.

The majority of these compounds have an outstanding importance in biochemistry and their functionalization widens their field of application.

For example, in the case of NAD+, but these considerations hold good also for the other members, its functionalized derivatives can be used, after having been attached by a covalent bond to macromolecules which are either water-soluble or water-insoluble, as non-diffusible coenzymes, or in affinity chromatography. Thus, in the case of attachment to water-soluble macromolecules, they can be used as non diffusible, water-soluble macromolecularized coenzymes. These permit the widening of the field of application of the known enzymic systems in which the enzyme is physically embedded in insoluble porous structures, such as fibers, polyacrylamide gel, microcapsules, etc. which are impervious to macromolecules. As a matter of fact, by physically embedding, together with the enzyme or a polyenzymic system also the water-soluble macromolecularized coenzyme, both the enzyme and the coenzyme remain in close contact and the scattering of the latter towards the outside of the occluding structure is prevented, while with the natural coenzyme this cannot be done on account of the low molecular weight of the latter. In the case of attachment of water-insoluble macromolecules they can be used for affinity chromatography or for enzymic reactions in a heterogeneous phase, it being possible to recover the coenzyme.

According to the present invention, the above mentioned derivatives which have been functionalized in the adenine nucleus are obtained by reacting the corresponding starting compound which has been halogen-substituted at the $C_8$ of the same nucleus, with the di-salt of an omega-mercaptocarboxylic acid having the general formula:

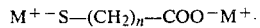

wherein $M^+$ is the ion of an alkali metal and n is an integer.

The reaction is conducted in aprotic polar solvents (such as hexamethyl-phosphotriamide, dimethyl sulphoxide and dimethylformamide) at a temperature ranging from $+20°$ C. to $+60°$ C., preferably at room temperature, and under anhydrous conditions.

The reaction causes a substitution of the halogen in the 8-position of the adenine nucleus in the manner shown by the formula:

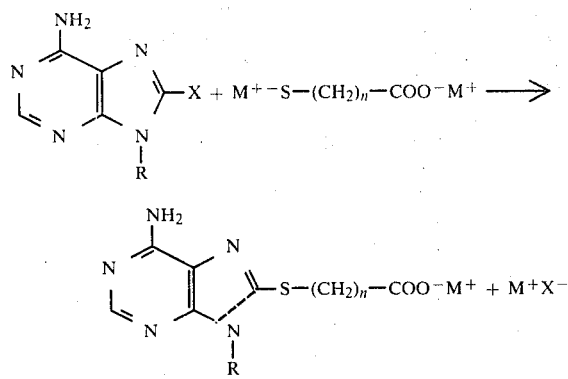

wherein n and $M^+$ have the meanings as indicated above, X is a halogen and R is the non-adenine residue of the compound.

The salt of the obtained carboxyl derivative is then converted during progress of the processing, into its corresponding free acid.

The method is absolutely general, but in the following portion of the disclosure, reference will be had to the reaction of the sodium bi-salt of the 3-mercaptopropionic acid with the derivatives of NAD+ and NADP+ which have been brominated at the 8-position carbon of the adenine nucleus of adenosine, with the aim of illustrating the methods which are required for carrying out said process.

It will be anyhow apparent, on reading the following, that anyone skilled in the art will be able to obtain functionalized adenine derivatives of the kind referred to above, starting from any 8-halogen adenine substrate by merely adapting the working conditions to the nature of the starting compound, without departing from the scope of the present invention.

This invention is also concerned with the preparation of macromolecularized adenine derivatives and the products obtained thereby, these latter containing one or more units having the general formula:

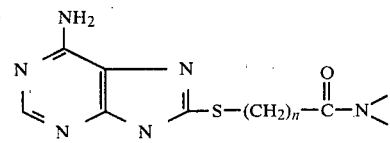

wherein n is an integer, and the radical

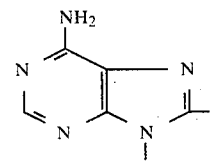

can be obtained from any compound having adenine nucleus, such as, for example, nicotinoylamide-adenine dinucleotide, nicotinoylamide-adenine dinucleotide phosphate, adenosine monophosphate, cyclic adenosine monophosphate, adenosine biphosphate, adenosine triphosphate, adenosine, adenine and wherein the nitrogen atom bound to the CO group is a part of a compound having a high molecular weight and which is either water-soluble or water-insoluble and contains one or more primary or secondary aminic groups (for example: polylysine, omega-aminoalkylpolyacrylamides, polysaccharide esters of omega-aminoalkylcarbamic acids, polyvinylamine, omega-aminoalkyl esters, or omega-aminoalkyl amides of the polyglutamic acid, aminoalkylsilanized glass microspheres, polyethyleneimine and others). Such functionalized compounds can react with at least one polymer having at least a primary or secondary aminic group, to give the macromolecularized adenine derivatives mentioned above, in the presence of a water-soluble carbodiimide (for example N-ethyl-N'-(3-dimethylaminopropyl)-carbodiimide hydrochloride) or an insoluble one (for example: N,N'-dicyclohexylcarbodiimide) as a condensing agent.

The condensation reaction between the carboxyl group of the functionalized adenine derivative and the aminic group of the macromolecule to give the amidic bond, is carried out in an aqueous environment or in a mixture of water and a water-soluble organic solvent (for example: pyridine, tetrahydrofuran, dioxan and others) at a temperature comprised between $+5°$ C. and $+50°$ C.; and preferably at room temperature.

The macromolecularized adenine derivatives which are the subject-matter of the present invention, have a number of applications.

For example, in the case of the macromolecularized derivatives of the nicotinoylamide-adenine dinucleotide (NAD), but the same is true of the other macromolecularized derivatives, they find application in affinity chromatography or as active, non-diffusible coenzymes.

Thus, in the case of attachment to water-soluble macromolecules, they can be used as non-diffusible, water-soluble macromolecularized coenzymes. These permit the widening of the field of application of the known enzymic systems in which the enzyme is embedded physically in insoluble structures, such as fibers, polyacrylamide gels, microcapsules and others, which are impervious to the macromolecules. As a matter of fact, by physically embedding together with the enzyme, or the polyenzymic system, also the water-soluble macromolecularized coenzyme, both the enzyme and the coenzyme remain in close contact and the scattering of the coenzyme towards the outside of the occluding structure is prevented, whereas, with the natural coenzyme, this cannot be done due to its low molecular weight.

In the case of attachment to water-insoluble macromolecules, they can be used for affinity chromatography or for enzymic reactions in a heterogeneous phase, it being possible to recover the coenzyme.

EXAMPLE No. 1

Preparation of the 8-(2-carboxyethylthio)adenosine

To a solution of 380 milligrams (1.1 millimol) of 8-bromoadenosine in 5 mls of anhydrous phosphotriamide there are added with stirring at room temperature and in an anhydrous atmosphere (nitrogen), 633 milligrams (4.2 millimols) of the sodium disalt of 3-mercaptopropionic acid (obtained by treating at room temperature the mercaptoacid with a stoichiometric amount of sodium hydride in anhydrous tetrahydrofuran and subsequent withdrawal of the solvent under vacuum).

After 16 hours of stirring at room temperature, the mixture is filtered and the filtrate is supplemented with 15 mls of water and extracted several times with chloroform until hexamethylphosphotriamide has been discharged.

The aqueous solution adjusted to a pH 8.5 with diluted HCl, is chromatographed on DOWEX-1 (HCOO$^-$) eluting with a gradient of formic acid in water. The fractions with $\lambda_{max}$ 282 mm are combined and freeze-dried to give 327 milligrams of 8-(2-carboxyethylthio)-adenosine.

The product proves to be pure at thin layer analysis (silica gel with a fluorescence indicator; eluent; isopropanol-water-32% ammonia in the volume ratios of 7:2:1; visualization of the spot by a UV lamp at 254 nm; RF=0.56) and also at high-voltage electrophoresis (Whatman paper 3MM 11×57 cm; electrolyte 0.02 M ammonium acetate pH 5.0, potential 5000 V during 40 mins., visualization of the spot with a UV lamp at 254 nm; the mobility of the product towards the anode is in agreement with the presence of the carboxyl group whereas adenosine migrates towards the cathode).

The UV spectrum in 0.1 M NaOH exhibits peak absorbance at 282 nm whereas that of 8-bromoadenosine is at 263 nm.

The $^1$H NMR in NaO$^2$H shows, in addition to the signals relative to adenosine with the exclusion of that of the proton at the 8-position, those relative to the protons of the side chain: 2.88 (2H, t; CH$_2$COO) and 3.86 (2H, t; CH$_2$S).

Also the mass spectrum confirms the structure attributed to the product (m/e 239, 221, 192, 167).

EXAMPLE No. 2

Preparation of the nicotinoylamide-8-(2-carboxyethylthio) adenine dinucleotide

To 118 milligrams (160 micromols) of nicotinoylamide-8-bromoadenine dinucleotide dissolved in 2 mls of anhydrous dimethylsulphoxide there are added with stirring at room temperature and under an anhydrous atmosphere (nitrogen), 98.4 milligrams (656 micromols) of the sodium disalt of the 3-mercaptopropionic acid (prepared as described in Example 1).

After 16 hours of stirring at room temperature, the mixture is filtered and ten volumes of acetone are added to the filtrate.

The obtained precipitate, separated by centrifugation and washed with acetone, is dried in a vacuo and dissolved in 15 mls of 0.1 M HCL. The solution, as adjusted to a pH of 7.5 with diluted soda, is chromatographed on DOWEX-1 (HCCO$^-$) by eluting with a gradient of formic acid in water.

The chromatographic fractions with $\lambda_{max}$ 276.5 are combined and freeze-dried to give 90 milligrams of nicotinoylamide 8-(2-carboxyethylthio) adenine dinucleotide. The product proves to be pure at the thin layer analysis silica gel with fluorescence indicator; eluent: isobutyric acid-water-32% ammonia in the volume ratios of 66:33:1.7; visualization of the spot with an UV lamp at 254 nm; Rf 0.31), and at high-voltage electrophoresis (3MM Whatman paper 11 by 57 cm; electrolyte: 0.02 M ammonium acetate, pH 5.0, potential 5,000 V during 30 minutes; visualization of the spot by UV lamp at 254 nm; mobility towards the anode greater than that of NAD$^+$, consistently with the presence of the carboxyl group).

The Ultraviolet spectrum in a solution of pyrophosphate buffer, pH 8.7, shows a peak at 276.5 nm which, by enzymic reduction with alcohol dehydrogenase from yeast, passes to 282 nm with the appearance of a new peak at 340 nm which is characteristic of the reduced nicotinoylamide nucleus.

The $^1$H NMR in $^2$H$_2$O shows, in addition to the signals relative to NAD$^+$ with the exclusion of that of the proton attached to the carbon in the 8-position of the adenine nucleus, those relative to the protons of the side chain: δ2.88 (2H,t; CH$_2$COO) and 3.86 (2H, t; CH$_2$S). Also the mass spectrum is in agreement with the structure attributed to the product (m/e 221, 192, 167).

EXAMPLE No. 3

Preparation of the nicotinoylamide-8-2-carboxyethylthio) adenine dinucleotide phosphate To 50 milligrams (57.6 micromols) of nicotinoylamide-8-bromoadenine dinucleotide phosphate dissolved in 1 ml of anhydrous dimethylsulphoxide, there are added with stirring at room temperature and in an anhydrous atmosphere (nitrogen), 36 milligrams (240 micromols) of the sodium disalt of the 3-mercaptopropionic acid (prepared as described in Example 1).

After 16 hours of stirring at room temperature, the mixture has been filtered and the filtrate is supplemented with ten volumes of acetone. The as-obtained precipitate, separated by centrifugation and washed with acetone, is dried in a vacuo and dissolved in 10 mls of 0.1 M HCl.

The solution, adjusted to pH 7.5 with diluted soda, is chromatographed on DOWEX-1 (Cl$^-$) by eluting with a gradient of CaCl$_2$ in water which has a pH of 3 by addition of HCl. The chromatographic fractions containing the expected product are combined, concentrated to a small volume, and desalified by gelfiltration on Sephadex G-10 by eluting the product with water.

The characterization of the nicotinoylamide-8-(2-carboxyethylthio) adenine dinucleotide phosphate is carried out similarly to what has been described in Example 2 for the corresponding derivative of the NAD$^+$ (glucose-6-phosphate dehydrogenase has been used for the enzymic reduction).

EXAMPLE No. 4

Preparation of the nicotinoylamide-8-(polyethyleneimine-3-carbonylethylthio) adenine dinucleotide

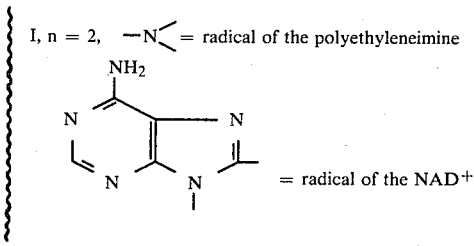

To 0.76 mls of an aqueous solution of polyethyleneimine (33% conc. weight/volume) adjusted to a pH of 5 with conc. HCl, there are added 39 milligrams of nicotinoylamide-8-(carboxyethylthio) adenine dinucleotide

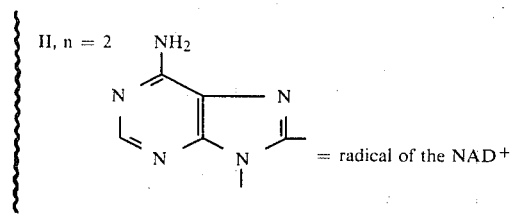

dissolved in 0.5 ml of water and 40 milligrams of N-ethyl-N'-(3-dimethyl-aminopropyl)-carbodiimide hydrochloride dissolved in 0.5 mls of water.

The reaction mixture, adjusted to a pH of 4.8 by addition of 2 M HCl is stirred at room temperature during 48 hours maintaining the pH at 4.8 during the first three hours by addition of 0.1 M HCl. The reaction mixture diluted with water to 20 mls is then transferred to a centrifugation tube and precipitated with 20 mls of 1 M phosphate buffer at a pH of 6. Centrifugation for 10 minutes is effected at 39,000 g and the solution is stripped of the polymeric precipitate by decantation.

In order further to purify the polymer, the latter is dissolved in 4 mls of a 2 M solution in NaCl and 0.05 M in acetate buffer at a pH of 5.5 and the solution thus obtained is supplemented by 16 mls of water and precipitated again with 20 mls of 1 M phosphate buffer at pH 6 and centrifuged during 10 minutes at 39,000 g by collecting the polymer by decantation.

Such a purification procedure is repeated for at least four times.

The product redissolved in a 2 M solution in NaCl and 0.5 M in acetate buffer at pH 5.5, is dialized against portions of 1 l of 1.10$^{-4}$ M HCl during four days, changing the solution every day.

By freeze drying the residue of the dialysis, there are obtained 223 milligrams of the polymeric derivative of NAD, $_{max}$ 276.5 nm.

The determination of the total NAD bound to the polymer is carried out by the measurement of the absorbance at 276.5 nm by assuming an extinction coefficient equal to that of the NAD derivative II ($\epsilon$18800 M$^{-1}$ cm$^{-1}$.

The determination of the coenzymically active NAD bound to the polymer is effected by quantitative enzymic reduction with alcohol dehydrogenase from yeast in a 0.1 M tris buffer at pH 9 in the presence of 0.2 M ethanol and 0.5 M semicarbazide hydrochloride.

From the spectrophotometric measure at 340 nm of NADH derivative which has been formed, the result is that 115 micromols of enzymically reducible NAD are bound to each gram of the polymer, and correspond to 90% of the total NAD bound to the polymer.

The thus obtained macromolecularized NAD is coenzymically active with several dehydrogenase. For example, with alcohol dehydrogenase from yeast, the speed of enzymic reduction of the macromolecularized NAD is 50% relative to that of the natural coenzyme. The determination is carried out in the following incubation mixture (1.0 ml): tris. HCl, 83 micromols, ethanol 166 micromols, semicarbazide, HCl, 42 micromols; coenzyme 0.1 micromol (exposed as bound and enzymically reducible NAD); enzyme 0.2 micrograms; pH 9.0; incubation temperature 25° C. The reduction speed is determined by the increase of the absorbance at 340 nm.

EXAMPLE 5

Preparation of the nicotinoylamide-8-(polylysine-2-carbonylethylthio) adenine dinucleotide

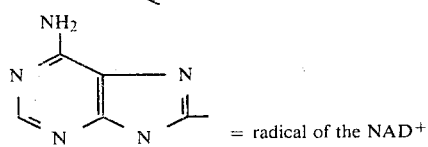

I, n = 2   —N< = a radical of polylysine

= radical of the NAD+

To 50 milligrams of polylysine hydrobromide having a mol. wt. of about 50,000 and dissolved in 0.5 mls of water, there are added 40 milligrams of nicotinoylamide-8-(carboxyethylthio) adenine dinucleotide.

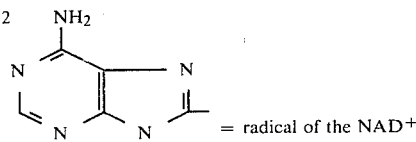

II, n = 2

= radical of the NAD+ dissolved in 0.5 ml of water, and 40 milligrams of N-ethyl-N'-(3-dimethylaminopropyl) carbo diimide hydrochloride dissolved in 0.5 ml of Water.

The reaction mixture, a justed to a pH of 4.7 with 0.1 M NaOH is stirred at room temperature during 24 hours while maintaining the pH at 4.7 during the first three hours by addition of 0.1 M HCl.

Under the same conditions there have been added 40 additional milligrams of carbodiimide in 0.5 ml of water and stirring is continued during 24 additional hours.

The reaction mixture diluted with water to a volume of 15 mls is then transferred to a centrifugation tube and precipitated with 10 mls of 0.15 M phosphate buffer at a pH of 6.

Centrifugation is carried out during ten minutes at 19,000 g and the solution of the polymeric precipitate is decanted.

To further purify the polymer, the latter is dissolved in 1 ml of a 2 M solution in NaCl and 0.05 M in acetate buffer at pH 5.5 and the thus obtained solution is supplemented with 15 mls of water and precipitated again with 10 mls of 0.15 M, pH 6, pyrophosphate buffer and centrifuged during 10 minutes at 39,000 g. collecting the polymer by decantation.

Such a purification procedure is repeated for at least four times. The product, redissolved in a 2 M solution in NaCl and 0.05 M in pH 5.5 acetate buffer, is dialized during 48 hours against 500 mls of a 3 M solution in NaCl.

Dialysis is then carried out against 2-mol portions of $1.10^{-4}$ M HCl during four days, the solution being daily renewed.

By freeze-drying the residue of the dialysis, there are obtained 34 milligrams of the polymeric derivative of NAD $_{max}$276.5.

The determination of the total NAD bound to the polymer is carried out by the measure of the absorbance at 276.5 nm, assuming an extinction coefficient equal to that of the derivative II of NAD ($\epsilon$18,800 $M^{-1}cm^{-1}$).

The determination of the coenzymically active NAD bound to the polymer is carried out by quantitative enzymic reduction with alcohol dehydrogenase from yeast in a 0.1 M tris buffer at pH 9 in the presence of 0.2 M ethanol and 0.05 M semicarbazide hydrochloride.

From the spectrophotometric measure at 340 nm of the as-formed NADH derivative, it appears that 157 micromols of enzymically reducible NAD are bound to each gram of polymer, corresponding to 90% of the total NAD bound to the polymer.

The thus obtained macromolecularized NAD is coenzymically active with several dehydrogenases.

EXAMPLE 6

Preparation of the nicotinoylamide-8-(aminohexyl-sepharose-2-carbonylethylthio) adenine dinucleotide

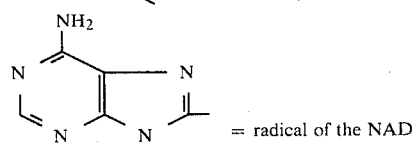

I, n = 2   —N< = radical of aminohexylsepharose 4β

= radical of the NAD 500 milligrams of aminohexyl sepharose 4B are allowed to swell with a 0.5 M NaCl solution, then washed with 200 mls of 0.5 M NaCl and then with water. To the as-obtained gel, slurried in 2 mls of water, there are added 40 milligrams of nicotinoylamide-8-(carboxyethylthio) adenine dinucleotide.

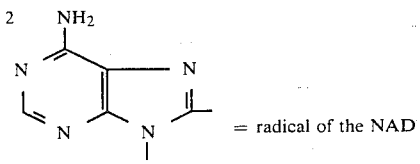

II, n = 2

= radical of the NAD dissolved in 0.5 ml of water and the pH is adjusted to 4.7 with 1 M NaOH. To the slurry stirred at room temperature with a mechanical stirrer, there are added 40 milligrams of N-ethyl-N'-(3-dimethylaminopropyl) carbodiimide hydrochloride dissolved in 0.2 ml water and stirring is continued during 24 hours while maintaining the pH at 4.7 during the first three hours by adding 0.1 M HCl.

Under the same conditions there are added at 24-hour intervals, three additional increments of the carbodiimide solution (40 milligrams in 0.2 ml of water) for a total reaction time of 96 hours. The gel is then filtered and washed with a 1 M solution in NaCl and $1.10^{-4}$ M in HCl until the disappearance of the UV absorption (not bound NAD) is experienced. There are thus obtained 1.8 ml of the polymeric derivative of NAD in the form of a moist gel, $\lambda_{max}$276.5 nm.

The UV spectrum has been obtained by suspending the gel in an aqueous 50% solution of sucrose (weight/weight) which delays the settling of the gel. The determination of the total NAD bound to the polymer is carried out by the measurement of the absorbance at 276.5 nm, assuming an extinction coefficient equal to that of the derivative II of NAD ($\epsilon 18,800$ M$^{-1}$cm$^{-1}$). The determination of the coenzymically active NAD bound to the polymer is carried out by quantitative enzymic reduction with alcohol dehydrogenase from yeast by suspending the gel in a 50% aqueous solution of sucrose (weight/weight) containing 0.1 M tris.HCl buffer, 0.2 M ethanol and 0.5 M semicarbazide hydrochloride, adjusted to a pH of 9.

From the photometric readings at 340 nm of the NADH derivative, it appears that 21 micromols of enzymically reducible NAD are bound to each gram of the dry product, that which corresponds to 80% of the total NAD bound to the polymer.

EXAMPLE 7

Preparation of the nicotinoylamide-8-(polyethyleneimine-2-carbonylethylthio) adenine dinucleotide phosphate

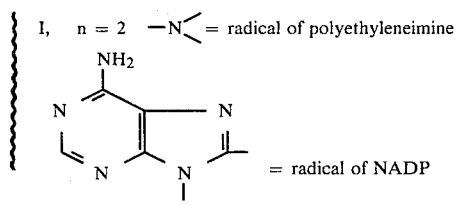

To 0.38 ml of a 33% aqueous solution of polyethyleneimine (weight/volume) adjusted to a pH of 5 with conc. HCl, there are added 20 milligrams of nicotinoylamide-8-(carboxyethylthio) adenine dinucleotide phosphate

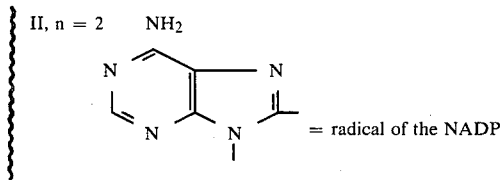

dissolved in 0.5 ml of water and 20 milligrams of N-ethyl-N'-(3-dimethylaminopropyl) carbodiimide hydrochloride dissolved in 0.2 ml of water. The reaction mixture, adjusted to a pH of 4.8 by addition of 2 M HCl, is stirred at room temperature during 24 hours by maintaining the pH at 4.8 during the first 3 hours by addition of 0.1 M HCl. Under the same conditions there are added 20 additional milligrams of carbodiimide in 0.2 ml of water and stirring is continued during 24 additional hours. The reaction mixture, diluted with water to a volume of 10 mls, is then transferred to a centrifugation tube and precipitated with 10 mls of 1 M phosphate buffer at a pH of 6. Centrifugation is carried out during 10 minutes at 39,000 g and the solution is stripped of the polymeric precipitate by decantation. To further purify the polymer, the latter is dissolved in 2 mls. of 2 M solution in NaCl and 0.05 M in pH 5.5 acetate buffer and the solution thus obtained is supplemented with 8 mls of water and precipitated again with 10 mls of 1 M, pH 6 phosphate buffer and centrifuged during 10 minutes at 39,000 g, the polymer being collected by decantation. Such a purification procedure is repeated for at least 4 times. The product, redissolved in a 2 M solution in NaCl and 0.05 M in pH 5.5 acetate buffer, is dialized against 1-liter portions of $1.10^{-4}$ M HCl during four days, the solution being renewed daily. By freeze-drying the residue of the dialysis there are obtained 83 milligrams of the polymeric derivative of the NADP, $\lambda_{max} 276.5$ nm. The determination of the total NADP bound to the polymer is carried out by measuring the absorbance at 276.5 nm, assuming an extinction coefficient equal to that of the derivative II of NAD ($\epsilon 18,000$ M$^{-1}$cm$^{-1}$).

The determination of the coenzymically active NADP bound to the polymer is carried out by quantitative enzymic reduction with glucose-6-phosphate dehydrogenase from yeast in 86.3 mM triethanolamine buffer, pH 7.6, containing 6.7 mM MgCl$_2$ and 1.2 mM glucose-6-phosphate. From the spectrophotometric measure at 340 nm of NADP derivative as formed, it appears that 23 micromols of enzymically reducible NADP are bound to each gram of polymer, that which corresponds to 20% of the total NADP bound to the polymer.

The thus obtained macromolecularized NADP is coenzymically active with several dehydrogenase such as for example 6-phosphogluconate dehydrogenase and L-glutamate dehydrogenase.

What we claim is:

1. A method for the preparation of macromolecularized adenine derivatives which comprises the steps of reacting a compound which contains a halogen atom in the 8-position and which has the formula,

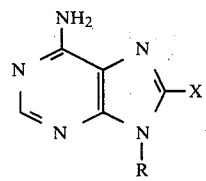

wherein X is a halogen and R is the non-adenine residue of the compound, with a di-alkali metal salt of an omega-mercaptocarboxylic acid at a temperature in a range of from about 20° C. to about 60° C. under anhydrous conditions and forming a functionalized adenine derivative compound, converting the functionalized adenine derivative compound to its corresponding free acid containing an adenine radical and having the formula

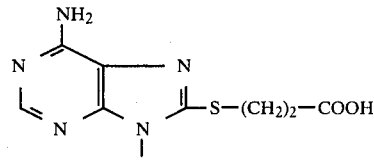

and in which the adenine radical is selected from the group consisting of nicotinoylamide adenine dinucleotide, nicotinoylamide adenine dinucleotide phosphate, adenosine triphosphate, adenosine diphosphate, adenosine monophosphate, adenosine, and adenine, and condensing the functionalized adenine free acid derivative with a polymer selected from the group consisting of polysine, omega-aminoalkyl polyanilamides, polysaccharide esters of omega-aminoalkyl carbamic acids, polyvinyl-amine, omega-aminoalkyl esters and omega-aminoalkylamides of polyglutamic acid, aminoalkyl silanized glass microsphenes, and polyethyleneimine in the presence of a condensing agent selected from water-soluble or insoluble carbodiimides in an aqueous environment or in a mixture of water and water-soluble organic solvent at a temperature between 5° C. and 50° C.

2. A method according to claim 1 for the preparation of nicotinoylamide-8-(polyethyleneimine-3-carboxyethylthio) adenine dinucleotide which comprises reacting nicotinoylamide-8-(carboxyethylthio) adenine dinucleotide with polyethyleneimine.

3. A method according to claim 1 for the preparation of nicotinoylamide-8-(polysine-2-carbonylethylthio) adenine dinucleotide which comprises reacting nicotinoylamide-8-(carboxyethylthio) adenine dinucleotide with polysine.

4. A method according to claim 1 for the preparation of nicotinoylamide-8-(aminohexyl-sephrose-2-carbonylethylthio) adenine dinucleotide which comprises reacting nicotinoylamide-8-(carboxyethylthio) adenine dinucleotide with aminohexyl sepharose 4B.

5. A method according to claim 1 for the preparation of nicotinoylamide-8-(polyethyleneimine-2-carbonylethylthio) adenine dinucleotide phosphate which comprises reacting nicotinoylamide-8-(2-carboxyethylthio) adenine dinucleotide phosphate with polyethyleneimine.

* * * * *